(12) United States Patent
Magdanz et al.

(10) Patent No.: US 9,883,889 B2
(45) Date of Patent: Feb. 6, 2018

(54) METHOD FOR THE CONTROLLED MOVEMENT OF MOTILE CELLS IN LIQUID OR GASEOUS MEDIA

(71) Applicant: LEIBNIZ-INSTITUT FUER FESTKOERPER UND WERKSTOFFFORSCHUNG DRESDEN E.V., Dresden (DE)

(72) Inventors: Veronika Magdanz, Dresden (DE); Samuel Sanchez, Dresden (DE); Oliver G. Schmidt, Dresden (DE)

(73) Assignee: LEIBNIZ-INSTITUT FUER FESTKOERPER UND WERKSTOFFFORSCHUNG DRESDEN E.V., Dresden (DE)

( * ) Notice: Subject to any disclaimer, the term of this patent is extended or adjusted under 35 U.S.C. 154(b) by 175 days.

(21) Appl. No.: 14/408,126

(22) PCT Filed: Jul. 5, 2013

(86) PCT No.: PCT/EP2013/064222
§ 371 (c)(1),
(2) Date: Feb. 26, 2015

(87) PCT Pub. No.: WO2014/012801
PCT Pub. Date: Jan. 23, 2014

(65) Prior Publication Data
US 2015/0164554 A1    Jun. 18, 2015

(30) Foreign Application Priority Data
Jul. 16, 2012    (DE) .................. 10 2012 212 427

(51) Int. Cl.
A61B 17/43    (2006.01)
C12N 5/071    (2010.01)
(Continued)

(52) U.S. Cl.
CPC .............. *A61B 17/43* (2013.01); *A61D 19/02* (2013.01); *C12N 5/0612* (2013.01); *A61B 2017/00876* (2013.01)

(58) Field of Classification Search
CPC ..... A61B 17/425; A61B 17/43; A61B 17/435; A61B 2090/3954; C12N 5/061;
(Continued)

(56) References Cited

U.S. PATENT DOCUMENTS

| 6,695,766 B2 | 2/2004 | Moruzzi et al. | |
| 2006/0264690 A1* | 11/2006 | Ochi | A61K 41/00 600/9 |
| 2010/0068808 A1* | 3/2010 | Bangera | B82Y 30/00 435/375 |

FOREIGN PATENT DOCUMENTS

WO    WO2012052486    *    4/2012    ............. A61N 2/004

OTHER PUBLICATIONS

Rakhi K Jha et al., "Smart RISUG: A potential new contraceptive and its magnetic field-mediated sperm interaction", International Jounal of Nanomedicine, 2009, pp. 55-64.
(Continued)

*Primary Examiner* — Charles A Marmor, II
*Assistant Examiner* — Carrie R Dorna
(74) *Attorney, Agent, or Firm* — Greenblum & Bernstein, P.L.C.

(57) ABSTRACT

The invention concerns the domains of materials science and medicine and relates to a method such as can be applied to in vivo or in vitro fertilization, for instance. The problem addressed by the present invention is that of specifying a method with which the activity and controlled mobility of motile cells is improved and the absorption of materials alien to the cell is prevented as far as possible. The problem is solved by a method in which one or more motile cells are introduced into or attached to one or a plurality of magnetic
(Continued)

particles, and subsequently the magnetic particles with the motile cells introduced into them or attached to them are moved in a directional manner by the application of an external magnetic field. The problem is further solved by the use of the method for the controlled movement of motile cells in liquid or gaseous media in the body of a mammal or human being.

17 Claims, 2 Drawing Sheets

(51) Int. Cl.
A61D 19/02 (2006.01)
A61B 17/00 (2006.01)

(58) Field of Classification Search
CPC ........ C12N 5/0612; A61N 2/00; A61N 2/002; A61N 2/004; A61N 2/02; A61N 2/06; A61N 2/12
See application file for complete search history.

(56) References Cited

OTHER PUBLICATIONS

Viroj Wiwanitkit et al., "Effect of gold nanoparticles on spermatozoa: the first world report", Fertility and Sterility, 2009, pp. 1-2.
Enver Kerem Dirican et al., "Clinical outcome of magnetic acitivated cell sorting of non-apoptotic spermatozoa before density gradient centrifugation for assisted reproduction", J Assist Genet, 2008, pp. 375-381.
Yongfeng Mei et al., "Versatile Approach for Integrative and Functionalized Tubes by Strain Engineering of Nanomembranes on Polymers", Advanced Materials, 2008, pp. 4085-4090.
Ekaterina I. Galanzha et al., "In vivo magnetic enrichment and multiplex photoacoutic detection of circulating tumour cells", nature nanotechnology, 2009, pp. 855-860.
Eniko Kadar et al., "Stabilization of Engineered Zero-Valent Nanoiron with Na-Acrylic Copolymer Enhances Spermiotoxicity", Environmental Sience & Technology, 2011, pp. 3245-3251.
K. Anslinger et al., "Application of sperm-specific antibodies for the separation of sperm from cell mixtures", Forensic Science Interantional: Genetics Supplement Series 1, 2008, pp. 394-395.

* cited by examiner

METHOD FOR THE CONTROLLED MOVEMENT OF MOTILE CELLS IN LIQUID OR GASEOUS MEDIA

CROSS-REFERENCE TO RELATED APPLICATIONS

The present application is a U.S. National Stage of International Patent Application No. PCT/EP2013/064222 filed Jul. 5, 2013, and claims priority of German Patent Application No. 10 2012 212 427.6 filed Jul. 16, 2012.

BACKGROUND OF THE INVENTION

1. Field of the Invention

The invention concerns the fields of materials science, biology and medicine and relates to a method for the controlled movement of motile cells in liquid or gaseous media, such as can be applied to in vivo fertilization or in vitro fertilization, for example.

2. Discussion of Background Information

In the case of low mobility of cells, for example, spermatozoa, different methods are known for achieving fertilization both in the body and outside the body and/or for improving the success rate thereof.

A method is known in which an egg or an embryo is provided with a layer of magnetic particles and, by an application of a magnetic field using a permanent magnet or an electromagnet, the egg or the embryo is transported into the uterus and stabilized there (U.S. Pat. No. 6,695,766 B4). To do this, magnetic particles are provided with reactive groups on their surface. The magnetic particles can have a diameter of 0.1 μm to 200 μm. These magnetic particles are joined with the egg or the embryo so that the reactive groups of the magnetic particles can react with the reactive groups on the surface of the egg or of the embryo.

Methods in which magnetic particles on the magnitude of nanometers are used have the disadvantage that the magnetic particles can be absorbed by the cells and thus, particularly in the case of sperm cells, cause toxicity (Subiai et al., Environ. Sci. Technol. 2011, Vol. 45; Rojanathathanes, et al., Fertility and Sterility, 2007, Vol. 91).

Furthermore, methods are known for the production of magnetic microtubes which are produced by means of a rolling-up of thin magnetic layers (Mei, Y. F., et al., Adv. Mater., 2008, Vol. 20). For this purpose a glass substrate, for example, is coated with a photoresist, which is irradiated with UV light for 7 seconds, wherein square structures are produced by means of a template and the unwanted photoresist regions are removed using a solvent. The substrate with the photoresist structures is coated with magnetic materials and again placed in a solvent, whereby the photoresist structures are then removed (sacrificial layer), which leads to the rolling-up of the Ti/Fe layers to form microtubes.

SUMMARY OF THE EMBODIMENTS

The object of the present invention is to provide a method for the controlled movement of motile cells in liquid or gaseous media with which the activity and guided mobility of motile cells is improved and the absorption of non-cellular materials is prevented to the greatest possible extent.

The object is attained by the invention disclosed in the claims. Advantageous embodiments are the subject matter of the dependent claims.

In the method according to the invention for the controlled movement of motile cells in liquid or gaseous media, one or multiple cells are introduced into or attached to one or multiple magnetic particles and, subsequently, the magnetic particles with the motile cells introduced thereinto or attached thereto are moved in a directional manner by an application of an external magnetic field.

Advantageously, water, biological fluids and/or blood are used as a liquid medium and air is used as a gaseous medium.

Likewise advantageously, sperm cells are used as motile cells.

Further advantageously, magnetic particles of ferromagnetic or paramagnetic materials are used.

And also advantageously, magnetic particles of titanium, platinum iron, iron oxide, gold or glass or of alloys or combinations of these materials are used, wherein nonmagnetic particles coated with magnetic materials are used.

It is also advantageous if magnetic particles are used which on the inner and/or outer surface thereof comprise functional groups, such as mannosyl/carbohydrate groups or sperm-binding proteins.

It is further advantageous if magnetic particles in the shape of a tube, a rod, a sphere, a hollow sphere, an asymmetrical body, an irregularly shaped hollow body or a network are used.

It is likewise advantageous to use magnetic particles having dimensions that are adapted to the size of the motile cell or cells or are embodied only slightly larger or smaller, wherein magnetic particles having dimensions of 200 nm to several micrometers are more advantageously used.

And it is also advantageous if microtubes or rolled-up microtubes are used as magnetic particles.

Furthermore, it is advantageous if an external magnetic field is achieved by a permanent magnet or electromagnet.

And it is also advantageous if the motile cells with the magnetic particles are moved in a controlled manner in a liquid which is located in vitro or in vivo.

It is likewise advantageous if magnetic particles with motile cells that are chemically or mechanically bonded to the magnetic particles are moved in a controlled manner.

Furthermore, it is advantageous if the magnetic particles with the motile cells introduced thereinto or attached thereto, which motile cells have not been used as intended, are moved to another location in a controlled manner by the applied external magnetic field.

According to the invention, the use of the motile cells moved in a controlled manner using the method according to the invention occurs in liquid or gaseous media in the body of a mammal or human being.

Advantageously, the use of the sperm cells moved in a controlled manner with the method according to the invention occurs in the uterus and/or in the fallopian tube.

With the method according to the invention for the controlled movement of motile cells in liquid or gaseous media, the activity and guided mobility of motile cells can for the first time be improved without the presence of non-cellular materials that could be absorbed by the cells.

This is achieved by having the motile cell or the motile cells introduced into or attached to a magnetic particle. The interaction between the motile cells and the magnetic particles is in particular achieved by the form of the magnetic particle, which is advantageously used in the shape of a tube, a rod, a sphere, a hollow sphere, an irregularly shaped body, an irregularly shaped hollow body or a network. Magnetic particles are thereby used which have dimensions that are adapted to the size of the motile cell or cells and are embodied only slightly larger or slightly smaller, that is, dimensions essentially in the micrometer range. Further advantageously, rolled-up microtubes are used as magnetic particles.

Iron, iron oxide, cobalt, titanium, platinum, gold or glass or alloys or combinations of these materials can advantageously be used as materials of the magnetic particles. In the event that these materials themselves do not have magnetic properties, or do not have magnetic properties to a sufficient extent, they are coated completely or partially with magnetic materials.

Furthermore, it is advantageous if the magnetic particles comprise on the inner and/or outer surface thereof functional groups. These functional groups can interact and/or react with functional groups on the surface of the motile cells and thus produce a physical and/or chemical bond which causes better adhesion of the motile cells on and in the magnetic particle and thus enables a secure transport of the magnetic particle with the motile cell(s).

However, it is equally possible that the inner and/or outer surface of the magnetic particles is designed in such a way that a mechanical bond between the magnetic particle and the motile cells is achieved, for example, by a rough surface of the magnetic particles.

Furthermore, the magnetic particle can also be formed asymmetrically or conically, for example, as a conically shaped microtube.

By means of the solution according to the invention, it is possible for the first time to control the movement of motile cells, that is, to guide the movement thereof in a desired direction.

Within the scope of this invention, motile cells are to be understood as meaning cells that autonomously have the capability of moving themselves in liquid or gaseous media. After the motile cell or the motile cells have been introduced into or onto one or multiple magnetic particle(s) and have been introduced into the liquid or gaseous medium, an external magnetic field can be applied and the direction of movement of the magnetic particles with the motile cells can be guided in a controlled manner by the movement of this field. An external magnetic field of this type can be produced by a permanent magnet or an electromagnet.

Particularly advantageously, the method according to the invention can be applied to support natural in vivo fertilization if sperm exhibit decreased mobility. An increased success rate for fertilizations is thus achieved, and an alternative reproductive technique is established, since a removal of the egg cell from the uterus is not necessary. The magnetic particles with sperm cells can be introduced directly into the uterus and the fallopian tubes. By means of the application of an external magnet, the sperm cell is thus directed to the egg cell in a targeted manner, and fertilization occurs.

The method according to the invention can, however, also be used for in vitro fertilization involving the transport of the cells to the egg cell outside the body.

In particular, the advantage of the solution according to the invention is that the magnetic particles cannot be absorbed by the cells and therefore have no negative effects on the cells.

BRIEF DESCRIPTION OF THE DRAWINGS

The following are thereby shown.

DETAILED DESCRIPTION OF THE EMBODIMENTS

Figure 1:
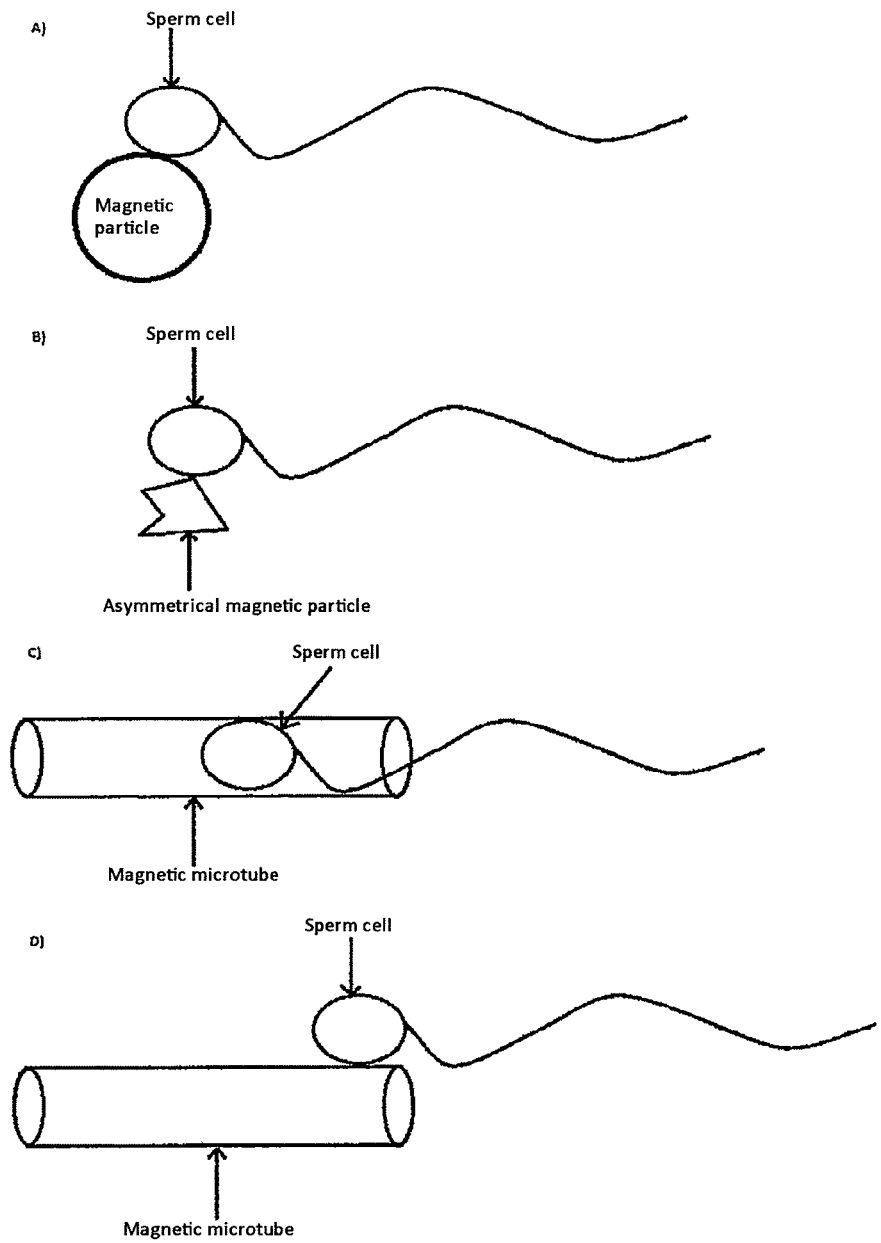
FIG. 1: Possibilities for an arrangement of a sperm cell on or in a magnetic particle in schematic form
Figure 2:
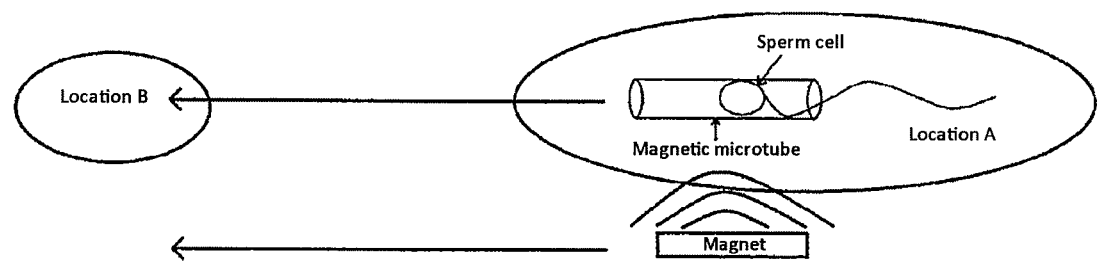
FIG. 2: The schematic functional principle of the controlled movement of a sperm cell in a microtube

Example $10^5$ Microtubes comprising an outer layer of 5 nm titanium, a middle 5-nm thick layer of iron and an inner 1-nm thick platinum layer, wherein the microtubes each have an inner diameter of 5 µm and a length of 50 µm and have been produced using a rolling-up technique. They are mixed together with 50 µL of sperm in 3 mL of human tubal fluid (HTF) medium. The sperm cells thereby interact with the microtubes, adhere to the outer surface thereof, and/or enter therein. After 5 min, the microtubes are bonded to one or up to three sperm cells. Through the use of magnets, desired combinations of sperm cells and microtubes can be selected under the microscope. Approximately 100 microtubes that are bonded to the sperm cells are brought into a spatially separate region in a targeted manner by the movement of the external magnet. This suspension is injected into the uterus. A permanent magnet is positioned outside the body, and the movement of the microtubes to the fallopian tube and the egg cells is guided by the movement of the permanent magnet. The successful transport of the sperm cell with the tube is tracked by ultrasound. The sperm can interact functionally with the egg cells through the openings of the microtubes and inseminate the egg cells. After the sperm cell has penetrated the egg cell, the microtubes are once again removed from the body through the movement of the permanent magnet.

The invention claimed is:
1. A method for the controlled movement of motile cells in liquid or gaseous media in a body of a mammal or human being, comprising:
   one of: introducing or attaching one or multiple motile cells, which autonomously move in liquid or gaseous media, into or to one or multiple magnetic particles and,
   while the one or multiple motile cells is/are autonomously moving in the liquid or gaseous medium, directionally guiding the autonomously moving one or multiple motile cells introduced into or attached to the one or more magnetic particles by an application of an external magnetic field, wherein the one or multiple motile cells are sperm cells.
2. The method according to claim 1, wherein the liquid medium comprises biological fluids and the gaseous medium comprises air.
3. The method according to claim 1, wherein the magnetic particles comprise ferromagnetic or paramagnetic materials.
4. The method according to claim 1, wherein the magnetic particles comprise titanium, platinum iron, iron oxide, gold or glass or alloys or combinations of these materials.
5. The method according to claim 4, wherein the magnetic particles comprise non-magnetic particles coated with magnetic materials.
6. The method according to claim 1, wherein the one or multiple magnetic particles comprise at least one of an inner and an outer surface functional group that includes one of:

at least one of a mannosyl and a carbohydrate group; or sperm-binding proteins.

7. The method according to claim 1, wherein the magnetic particles have a shape of a tube, a rod, a sphere, a hollow sphere, an asymmetrical body, an irregularly shaped hollow body or a network.

8. The method according to claim 1, wherein the magnetic particles have dimensions that are adapted to a size of the one or multiple motile cells.

9. The method according to claim 8, wherein the dimensions of the magnetic particles range from 200 nm to several micrometers.

10. The method according to claim 8, wherein the magnetic particles are dimensioned to be one of slightly larger or smaller than the one or multiple motile cells.

11. The method according to claim 1, wherein the magnetic particles comprise at least one of microtubes and rolled-up microtubes.

12. The method according to claim 1, wherein an external magnetic field is achieved via a permanent magnet or electromagnet.

13. The method according to claim 1, wherein the autonomously moving motile cells with the magnetic particles are guided in a controlled manner in a liquid which is located one of in vitro or in vivo.

14. The method according to claim 1, wherein the one or multiple motile cells are at least one of chemically and mechanically bonded to the one or multiple magnetic particles.

15. The method according to claim 1, wherein a portion of the multiple motile cells introduced into or attached to multiple magnetic particles are guided to another location in a controlled manner by the applied external magnetic field.

16. A method for controlled guidance of autonomously moving motile cells in liquid or gaseous media in a body of a mammal or human being, comprising:
    joining together at least one motile cell, which autonomously moves in the liquid or gaseous media, and at least one magnetic particle; and
    applying an external magnetic field to directionally guide the at least one motile cell joined to the at least one magnetic particle as the at least one motile cell autonomously moves through the liquid or gaseous media, wherein the at least one motile cell comprises a sperm cell.

17. The method according to claim 16, wherein the liquid or gaseous media comprises at least one of a uterus and a fallopian tube.

\* \* \* \* \*